United States Patent [19]

Shasha et al.

[11] Patent Number: 5,061,697

[45] Date of Patent: Oct. 29, 1991

[54] ADHERENT, AUTOENCAPSULATING SPRAY FORMULATIONS OF BIOCONTROL AGENTS

[75] Inventors: Baruch S. Shasha, Peoria; Michael R. McGuire, Metamora, both of Ill.

[73] Assignee: The United States of America as represented by the Secretary of Agriculture, Washington, D.C.

[21] Appl. No.: 389,090

[22] Filed: Aug. 3, 1989

[51] Int. Cl.$^5$ ............................ B01J 13/02; C12N 11/10
[52] U.S. Cl. ........................................ 514/60; 514/23; 514/54; 514/965; 514/778; 514/777; 71/3; 71/94; 424/405; 424/407; 424/408; 424/409; 424/410; 424/418; 424/439; 424/440; 424/488; 424/93; 264/4.1
[58] Field of Search ............... 514/23, 54, 60, 965, 514/777, 778; 71/3, 94; 424/488, 405, 407, 408, 409, 410, 418, 439, 440, 93; 264/4.1

[56] References Cited

U.S. PATENT DOCUMENTS

| | | | |
|---|---|---|---|
| 169,925 | 11/1875 | Steele | 424/410 |
| 212,835 | 3/1879 | Benton | 424/410 |
| 415,192 | 11/1889 | Evans | 424/439 |
| 2,363,852 | 11/1944 | Beekler | 424/410 |
| 2,813,058 | 11/1957 | Smith | 424/410 |
| 4,447,984 | 5/1984 | Sampson et al. | 47/58 |
| 4,645,682 | 2/1987 | Elmore | 47/58 |
| 4,678,669 | 7/1987 | Ricard | 47/58 |
| 4,701,326 | 10/1987 | Nelsen et al. | 424/410 |
| 4,859,377 | 8/1989 | Shasha et al. | 424/410 |

OTHER PUBLICATIONS

R. L. Dunkle et al., "Starch-Encapsulated, *Bacillus thuringiensis:* A Potential New Method for Increasing Environmental Stability of Entomopathogens," Environ. Entomol., 17(1): 120–126 (1988) (NRRC #5962), Feb. 1988.

D. Trimnell et al., "Autoencapsulation: A New Method for Entrapping Pesticides Within Starch," J. Controlled Rel., 7: 25–31 (1988) (NRRC #6000).

*Primary Examiner*—Ronald W. Griffin
*Attorney, Agent, or Firm*—M. Howard Silverstein; John D. Fado; Curtis P. Ribando

[57] ABSTRACT

Sprayable, starch-based formulations for autoencapsulating biological control agents, such as pathogenic bacteria and viruses, incorporate a sugary material to promote adherence of the encapsulated agent to treated foliage. The autoencapsulated pathogens are characterized by high survivability and are useful in controlling insects and other pest species.

15 Claims, No Drawings

ADHERENT, AUTOENCAPSULATING SPRAY FORMULATIONS OF BIOCONTROL AGENTS

BACKGROUND OF THE INVENTION

1. Field of the Invention

It has been estimated that entomopathogens, mainly *Bacillus thuringiensis* (*B.t.*), will reach a $100,000,000 market by 1992, approximately 90% of which will be sold as sprayable formulated material. Effectiveness of spray formulations is dependent on attractiveness to target pest insects and retention of pathogenic activity. This invention relates to a novel spray formulation, based on a renewable resource, which satisfies these criteria.

2. Description of the Prior Art

The use of starch has many attractive properties for biocontrol agent encapsulation. First, it is inert and will not alter resting stages of most living organisms; second, particulate or liquid UV-screening agents are easily added; third, its major component is amylopectin which is readily digested by most phytophagous pests possessing α-amylase enzymes [G. M. Chippendale et al., J. Insect Physiol. 20: 751-759 (1974); K. Nishide et al., J. Fac. Agric. Tottori Univ. 11: 12-22 (1976)]; and fourth, it is abundant and inexpensive compared to most other materials currently used in encapsulation [B. S. Shasha, In Controlled Release Technologies: Methods, Theory, and Applications, Vol. 2, A. F. Kydoniens (ed.), CRC Press, Inc., Boca Raton, Fla.].

Recently, Dunkle et al. [Environ. Entomol. 17: 120-126 (1988) and U.S. patent application Ser. No. 07/72,205 filed on July 10, 1987, now U.S. Pat. No. 4,859,377] prepared a granular formulation of *B.t.* encapsulated within a starch matrix. The advantage of this method over existing formulations is that it allows incorporation of various additives such as sunlight protectors to prevent solar inactivation and feeding stimulants to increase palatability and thereby reduce the amount of active ingredient necessary for control. Trimnell et al. [J. Controlled Release 7: 263-268 (1988)] have reported a sprayable herbicide formulation utilizing pregelatinized corn starch and flour. These sprays give a thin film of the formulation on plant leaves which autoencapsulates (encapsulates the active agent in situ) upon drying and thereby allows sustained release of active ingredient. However, within 2-3 days after application, these films peel away from the plant leaves. In general, sprayable formulations of *B.t.* lose activity within 2-4 days following application to plant foliage in the field [Morris, Can. Ent. 115: 1215-1227 (1983); Beegle et al., Environ. Entomol. 10: 400-401 (1981); Leong et al., Environ. Entomol. 9: 593-599 (1980)].

SUMMARY OF THE INVENTION

We have now unexpectedly discovered that when a sugary material is incorporated into a spray formulation in combination with a pregelatinized starchy material and a biocontrol agent, the sugary material acts as a sticking agent, and the resulting formulation is retained on plant leaves for a dramatically longer period of time.

In accordance with this discovery, it is an object of the invention to provide a facile, universal, and industrially acceptable formulation for autoencapsulation of sensitive biocontrol agents.

It is also an object of the invention that the primary matrix-forming material be derived from naturally renewable resources.

Another object of the invention is that the resulting encapsulation be characterized by high survivability of the active agent.

It is a further object of the invention that the encapsulated substance be controllably released to the target pests and resistant to losses by environmental conditions.

Other objects and advantages of this invention will become readily apparent from the ensuing description.

DETAILED DESCRIPTION OF THE INVENTION

Starch is a low-cost and abundant natural polymer composed of amylose and amylopectin. Amylose is essentially a linear polymer having a molecular weight in the range of 100,000-500,000, whereas amylopectin is a highly branched polymer having a molecular weight of up to several million. When starch is gelatinized in water and cooled, the amylose retrogrades to a much greater extent than the amylopectin fraction. Retrogradation is a term applied to the phenomenon whereby starch chains in dispersion associate, become insoluble, and precipitate. The rate and extent of retrogradation depend on properties of dispersion (pH, temperature, concentration) and on the amount of amylose present in the dispersion. Common corn starch (pearl) contains about 25% amylose and 75% amylopectin; whereas the waxy corn starches contain only amylopectin, and those referred to as high-amylose starch contain up to 75% amylose.

The starting encapsulating material for use in the invention includes any pregelatinized starch which will form a gel upon rehydration in an aqueous medium. Pregelatinized starches are commercially available and are prepared for example by cooking the starch at elevated temperatures and pressures in the presence of a lower alcohol. A preferred pregelatinized starch is a product sold commercially under the tradename "MIRA-SPERSE" which contains mostly amylopectin. Source materials for deriving the pregelatinized starch include pearl corn starch, potato starch, tapioca starch, flours containing these starches, as well as mixtures of these with waxy corn starch and high-amylose corn starch.

The sugary materials contemplated for use in the invention as sticking agents include sucrose, glucose, fructose, mannose, α-methyl glucoside, and various corn syrups. The amount of sugary material required is that amount which is effective to delay the peeling of the dried formulation from the target substrate. Ratios of starch:sugary material will typically range from about 1:2 to about 1:0.6, with ratios in the range of 1:1 to 1:0.6 being preferred.

The biocontrol agents contemplated for use herein include without limitation all bacteria, fungi, yeasts, viruses, microsporidians, protozoa, and other lower organisms which are pathogenic toward target pests. Of course any component of the organism or stage of its life cycle which is infective to the host upon ingestion is considered to be within the scope of the invention. For instance, in the case of *B.t.*, the vegetative cells, spores, and proteinaceous crystals are all effective in directly or indirectly killing host insects susceptible to *B.t.* It is also known that naturally occurring and synthetic vectors such as plasmids, phages, and various DNA/RNA constructs have potential for functionally modifying higher organisms, and therefore are also included herein as being within the scope of the term "biocontrol agent." Examples of other agronomically important pest pathogens besides $B.t.$ are $B.$ *sphaericus*, $B.$ *popillae*, microsporidians such as *Vairimorpha necatrix* and *Nosema locustae*, *Autographa californica* nuclear polyhedrosis virus, and *Heliothis* spp. virus, and the fungus *Beauveria bassiana*.

The target pests contemplated for control by means of the subject encapsulated agents include all species susceptible to the above-mentioned biocontrol agents. These characteristics are typical of most phytophagous (plant-eating) insects, especially those considered to be crop or tree pests.

Besides the active agent itself, other additives and adjuncts may be formulated into the subject compositions. Examples of these include dispersants, feeding stimulants (phagostimulants), UV protectants, preservatives, and inert fillers. Also of interest are agronomically acceptable carriers or vehicles for the active agent or any of the other components formulated into the encapsulated compositions.

In accordance with one embodiment of the invention, formulation of the biocontrol agent into a sprayable liquid is performed by dry-mixing the pregelatinized starchy material with the sugary material and combining this mixture with a dispersion of the entomopathogen in water. Vigorous stirring is usually required to disperse the starch in water. Alternatively, the starch material and/or the sugary material can be predispersed in water prior to combination with the entomopathogenic agent. The pregelatinized starchy material in aqueous dispersion must have a stable but low enough viscosity to be sprayable by conventional equipment. This property is characteristic of diluted starches and flours as well as starches and flours which have been partially degraded by chemical or physical means to the extent that the amylose chains will not spontaneously reassociate to a significant degree until their concentration in dispersion is raised above a certain threshold value. Thus, gel formation is retarded until evaporation of water from the sprayed composition causes the concentration of the degraded starch molecules to exceed the threshold, and then autoencapsulation occurs. Initial concentrations of the starch in the sprayable formulation should be in the range of about 1–10% by weight. In field application, droplets of the liquid adhere to the foliage surfaces and remain bound thereto even after gelling takes place.

In yet another embodiment of the invention, the biocontrol agent, pregelatinized starchy material, and the sugary material can be admixed and applied to the plant foliage as a dry formulation. The hygroscopic nature of the sugar enables the mixture to absorb moisture from the ambient. Moisture provided during periods of high humidity, dew, and rain will promote in situ formation of an aqueous dispersion of the formulation and gelling of the starchy material. Upon drying, autoencapsulation occurs as previously described.

The following examples are intended only to further illustrate the invention and are not intended to limit the scope of the invention which is defined by the claims.

EXAMPLE 1

Preparation of Formulations

Seven formulations given in Table I, and devoid of biocontrol agent were prepared for subsequent evaluation. The single dry component of Formulations 1–3 was dispersed in 300 ml of water using a Waring blender. Formulation 4 was prepared by pasting the dry component in the glycerol before dispersion in the water (supra). The dry components of Formulations 5–7 were thoroughly mixed dry before dispersion in the water.

The amount of material not dissolved and therefore likely to clog spray nozzles was measured by screening (0.7-mm diameter pores) the formulations and weighing the dried residues. Viscosity of the screened formulations was measured with a "Brookfield LVF" viscometer at 6 rpm and 21° C., 2 hr after initial mixing. The results are reported in Table II below. "MIRA-SPERSE" contains mostly amylopectin, whereas "MIRA-GEL" contains the same level of amylose (about 25%) as found in regular corn starch. "MIRA-SPERSE" (formulations 2 and 6) dispersed completely, did not retrograde to form clumps, and left no residue when screened. "MIRA-GEL" (1) and pregelatinized flour (3) retrograded somewhat to produce clumps which resulted in a residue on the screen. Furthermore, the protein of the pregelatinized flour did not dissolve well. The addition of glycerol to "MIRA-GEL" (4) alleviated the residue problem of this component, and sucrose reduced the amount of residue from "MIRA-GEL" (5) and flour (7). The viscosity of all formulations, including those containing "MIRA-SPERSE" (2 and 6), was well within the range required for sprayable materials.

EXAMPLE 2

($B.t.$) Viability in Formulations

Seven formulations were prepared as described in Example 1, then autoclaved, and cooled to room temperature. $B.t.$ (technical powder, 80,000 IU/mg, Abbott Laboratories, North Chicago, Ill.) was suspended in sterile water, and aliquots were thoroughly mixed into each of the formulations. The formulations containing the $B.t.$ were held for 0, 4, or 7 days at 2° C. after which samples were diluted and plated (10 μl) on the Semidefined Growth Medium for *Bacillus thuringiensis* of Luthy [Vierteljahrsschrift der Naturforschenden Gesellschaft in Zurich 120: 81–163 (1975)]. Following incubation for 24 hr at 28° C., colonies were counted. None of the liquid formulations tested were toxic to $B.t.$ spores, as shown by the results in Table III, which gives average numbers of colonies from diluted samples. An increase in colony counts over a 7-day period suggests the occurrence of spore germination and growth of vegetative cells.

EXAMPLE 3

Formulation Adherence to Leaf Surfaces

Cotton plants were obtained approximately 3 wks after seeding, when 2–4 true leaves had expanded. Upper surfaces of the leaves were treated with the seven formulations of Example 1. Coatings were applied by brushing the formulations onto the leaves with a 2.5-cm paint brush. After the leaves had dried, plants were subjected to one of two watering regimes: (1) plants were watered only to the soil or (2) plants were watered to the soil and to the foliage. Foliage watering was accomplished every 2 days by allowing water to flow from an 8-cm diameter nozzle with 1-mm perforations until runoff occurred. Estimates of the amount of applied material adhering to each leaf were made every 1-2 days by visual examination. The same individual made all the estimates throughout the experiment. The estimates are expressed as percent of applied material in Table IV (watered to soil only) and Table V (watered to soil and foliage).

The results show that the "MIRA-SPERSE"-sucrose formulation (Formulation 6) remained on leaves longer than any of the other formulations regardless of watering regime. "MIRA-SPERSE" alone (Formulation 2) quickly dried and flaked off the plant leaves when watering was to the soil, but the leaves retained approximately 50% of the applied material when watering was over the leaves. "MIRA-GEL" and pregelatinized flour without additives (Formulations 1 and 3, respectively) both lost material quickly regardless of watering regime. When watering was to the soil only, "MIRA-GEL" and flour combined with sucrose (Formulations 5 and 7, respectively) remained on the leaves for a longer period of time. When watering was over the leaves, material was not lost from these formulations until the fifth day after application. This compares to a loss of material within 3 days when sucrose was not present. The largest effect of sucrose was observed with "MIRA-SPERSE." When sucrose was present and watering was over the leaves, less than 5% of applied material was lost up to 13 days post-application. When watered to the soil only, material was not lost until day 20 of the experiment.

EXAMPLE 4

Effect of Sugar Type on Adherence of "MIRA-SPERSE" Formulations

Formulations of "MIRA-SPERSE" and the various sugars shown in Table VI in a 1:1 ratio were prepared as described in Example 1 for Formulations 5-7. The concentration of each component was 3.3%. The formulations were applied to cotton plants and evaluated for adherence by the procedure of Example 3 in which the plants were watered to the pot. The results are reported in Table VI below.

EXAMPLE 5

Effect of Sucrose Concentration on Adherence of "MIRA-SPERSE" Formulations

Formulations of "MIRA-SPERSE" and sucrose in various ratios were prepared as described in Example 1 for Formulations 5-7. The concentration of "MIRA-SPERSE" was 3%. The formulations were applied to cotton plants and evaluated for adherence by the procedure of Example 3 in which the plants were watered to the pot. The results are reported in Table VII below.

EXAMPLE 6

Effect of Corn Syrup Solids on Adherence of "MIRA-SPERSE" Formulations

Formulations of "MIRA-SPERSE" and corn sugars solids in various ratios were prepared as described in Example 1 for Formulations 5-7. The concentration of "MIRA-SPERSE" was 3%. The formulations were applied to cotton plants and evaluated for adherence by the procedure of Example 3. For each ratio, the plants were divided into two groups, one of which was watered to the soil only (pot), and the other to the soil and foliage (leaves). The results are reported in Table VIII below.

EXAMPLE 7-9

Bioassay of *B.t.*-Treated Leaves Against the European Corn Borer (ECB)

Formulations of "MIRA-SPERSE" and sucrose in a 1:1 ratio were prepared by dry mixing 1.5 g of each component and dispersing the mixture in 50 ml sterile water containing 3 mg *B.t.* technical powder (Example 7) or 20 mg "Dipel 2X" (Examples 8-9) (32,000 IU/*B.t.*/mg) using a Waring blender. The formulations were applied to cotton plants as described in Example 3. As a control, additional leaves were treated with water containing similar amounts of *B.t.* in the absence of an encapsulating system. Plants watered to the pot were compared to plants watered to the leaves. On the day of assay, leaves were excised and trimmed to fit 9-cm diameter petri dishes. Ten ECB larvae less than 12-hr old were added, filter paper was applied to the lid to absorb excess moisture, and the dish was sealed with two wraps of "Parafilm." Dishes were incubated at 28° C. in the dark for 3 days and then examined for live and dead larvae. Shapes of the individual curves were compared by analysis of variance and subsequent linear and quadratic contrasts. The results are reported in Table IX below.

It is understood that the foregoing detailed description is given merely by way of illustration and that modification and variations may be made therein without departing from the spirit and scope of the invention.

TABLE I

| | Test-Sprayable Test Formulations | | | | |
|---|---|---|---|---|---|
| Formulation No. | "MIRA-GEL"[a] (g/300 ml $H_2O$) | "MIRA-SPERSE"[b] (g/300 ml $H_2O$) | Flour[c] (g/300 ml $H_2O$) | Glycerol[d] (g/300 ml $H_2O$) | Sucrose[e] (g/300 ml $H_2O$) |
| 1 | 10 | | | | |
| 2 | | 10 | | | |
| 3 | | | 10 | | |
| 4 | 10 | | | 20 | |
| 5 | 10 | | | | 10 |
| 6 | | 10 | | | 10 |
| 7 | | | 10 | | 10 |

[a]Pregelatinized corn starch (industrial grade, C3-445, A. E. Staley Co.).
[b]Pregelatinized corn starch (industrial grade, C3-444, A. E. Staley Co.).
[c]Pregelatinized corn flour (12687, Illinois Cereal Mills, Inc.).
[d]ACS grade, Fisher Scientific.
[e]"Domino Confectioners 10-X Sugar," Amstar Sugar Corporation.

TABLE II

Physical Characteristics of Sprayable Formulations

| Formulation No. | Components | Residue (mg) | Viscosity (cp) |
|---|---|---|---|
| 1 | "MIRA-GEL" | 223 | 50 |
| 2 | "MIRA-SPERSE" | 0 | 3400 |
| 3 | corn-flour | 235 | 50 |
| 4 | "MIRA-GEL" + glycerol | 0 | 70 |
| 5 | "MIRA-GEL" + sucrose | 55 | 330 |
| 6 | "MIRA-SPERSE" + sucrose | 0 | 3400 |
| 7 | corn-flour + sucrose | 120 | 70 |

TABLE III

Viability of B.t. in Sprayable Test Formulations

| Formulation No. | Component | Days in contact with formulation 0 | 4 | 7 |
|---|---|---|---|---|
|  | water | .24.8 | 56.8 | 55.9 |
| 1 | "MIRA-GEL" | 19.2 | 50.9 | 102.6 |
| 2 | "MIRA-SPERSE" | 49.7 | 92.1 | 83.1 |
| 3 | corn-flour | 58.5 | 102.5 | 120.0 |
| 4 | "MIRA-GEL" + glycerol | 35.2 | 46.9 | 93.1 |
| 5 | "MIRA-GEL" + sucrose | 38.7 | 44.9 | 77.0 |
| 6 | "MIRA-SPERSE" + sucrose | 110.7 | 124.1 | 129.0 |
| 7 | corn-flour + sucrose | 95.8 | 104.4 | 123.6 |

TABLE IV

Percent of Original Material Remaining on Leaf Surface When Watered to Pot Only

| Days after application | 1 | 2 | 3 | 4 | 5 | 6 | 7 |
|---|---|---|---|---|---|---|---|
| 1 | 99 | 99 | 99 | 100 | 100 | 100 | 100 |
| 2 | 99 | 99 | 99 | 100 | 100 | 100 | 100 |
| 3 | 75 | 85 | 90 | 100 | 100 | 100 | 100 |
| 4 | 75 | 25 | 50 | 90 | 100 | 100 | 100 |
| 5 | 50 | 25 | 50 | 60 | 100 | 100 | 100 |
| 7 | 40 | 25 | 25 | 60 | 100 | 100 | 100 |
| 8 | 40 | 25 | 20 | 40 | 100 | 100 | 100 |
| 9 | 35 | 25 | 20 | 30 | 100 | 100 | 100 |
| 11 | 35 | 10 | 10 | 30 | 90 | 100 | 100 |
| 13 | 35 | 10 | 10 | 30 | 90 | 100 | 100 |
| 15 | 35 | 10 | 10 | 20 | 85 | 100 | 95 |
| 18 | 25 | 10 | 10 | 20 | 60 | 100 | 90 |
| 20 | 20 | 10 | 10 | 20 | 60 | 95 | 90 |

TABLE V

Percent of Original Material Remaining on Leaf Surface When Watered to Pot and Leaves

| Days after application | 1 | 2 | 3 | 4 | 5 | 6 | 7 |
|---|---|---|---|---|---|---|---|
| 1 | 99 | 99 | 99 | 100 | 100 | 100 | 100 |
| 2 | 99 | 99 | 99 | 100 | 100 | 100 | 100 |
| 3 | 85 | 90 | 99 | 90 | 99 | 100 | 100 |
| 4 | 50 | 60 | 50 | 70 | 98 | 98 | 100 |
| 5 | 40 | 60 | 20 | 65 | 60 | 98 | 20 |
| 7 | 40 | 50 | 10 | 50 | 40 | 98 | 10 |
| 8 | 35 | 50 | 10 | 50 | 50 | 98 | 10 |
| 9 | 30 | 50 | 0 | 50 | 50 | 98 | 10 |
| 11 | 30 | 50 | 0 | 30 | 30 | 98 | 10 |
| 13 | 30 | 50 | 0 | 30 | 30 | 80 | 10 |
| 15 | 30 | 50 | 0 | 25 | 40 | 70 | 10 |
| 18 | 20 | 50 | 0 | 10 | 30 | 70 | 10 |
| 20 | 20 | 40 | 0 | 10 | 30 | 70 | 5 |

TABLE VI

Effect of Sugar Type on Adherence of "MIRA-SPERSE" Formulations

| Days after application | % of Original material remaining on plant | | | | | | |
|---|---|---|---|---|---|---|---|
|  | M. glucoside | Glucose | Mannose | Fructose | Sucrose | Mannitol | None |
| 5 | 100 | 100 | 100 | 100 | 100 | 95 | 65 |
| 7 | 100 | 100 | 100 | 100 | 100 | 60 | 55 |
| 11 | 100 | 95 | 100 | 100 | 100 | 20 | 25 |
| 14 | 95 | 95 | 100 | 100 | 100 | 25 | 20 |
| 17 | 90 | 95 | 100 | 100 | 100 | 20 | 20 |

TABLE VII

Effect of Sucrose Concentration on Adherence of "MIRA-SPERSE" Formulations

| Days after application | % of Original material remaining on plant "MIRA-SPERSE":sucrose | | | | |
|---|---|---|---|---|---|
|  | 10:10 | 10:6 | 10:4 | 10:2 | 10:0 |
| 6 | 100 | 100 | 50 | 30 | 30 |
| 10 | 100 | 100 | 50 | 30 | 25 |
| 13 | 100 | 100 | 50 | 20 | 25 |

TABLE VIII

Effect of Corn Syrup Solids on Adherence of "MIRA-SPERSE" Formulations

| Days after application | % of Original material remaining on plants "MIRA-SPERSE":corn syrup solids | | | | | | | | | |
|---|---|---|---|---|---|---|---|---|---|---|
|  | 10:10 | | 10:7.5 | | 10:5 | | 10:2.5 | | 10:0 | |
|  | Pot | Leaf | Pot | Leaf | Pot | Leaf | Pot | Leaf | Pot* | Leaf |
| 5 | 95 | 100 | 85 | 100 | 70 | 100 | 85 | 100 | ... | 100 |
| 9 | 85 | 100 | 50 | 95 | 25 | 95 | 10 | 85 | ... | 90 |
| 12 | 70 | 100 | 50 | 95 | 25 | 95 | 10 | 85 | ... | 90 |
| 14 | 70 | 100 | 50 | 95 | 25 | 95 | 10 | 85 | ... | 90 |

*Not done.

TABLE IX

Bioassay of Leaves Treated with B.t. and Exposed to Different watering Regimes

| Example (conclusions $P < 0.05$)[2,3] | Amount of B.t. (IU/ml) | Days PA | Mean % mortality (Reps)[1] | | | | |
|---|---|---|---|---|---|---|---|
| | | | Encapsulated | | | Not encapsulated | |
| | | | Leaves | Pot | Watered to | Leaves | Pot |
| 7 (A,B,C,D) | 40,000 | 1 | 100(5) | 100(5) | | 100(5) | 100(5) |
| | | 8 | 98(10) | 95(10) | | 46(10) | 38(10) |
| | | 15 | 35(5) | 100(5) | | 15(4) | 7.5(4) |
| 8 (B,C,D) | 12,800 | 0 | 94(5) | 88(5) | | 72(5) | 66(5) |
| | | 7 | 79(10) | 83(10) | | 20(6) | 25(10) |
| | | 14 | 50(5) | 44(5) | | 14(5) | 0(5) |
| 9 (A,B,C,D) | 12,800 | 1 | 99(10) | 100(10) | | 90(10) | 91(10) |
| | | 8 | 79(10) | 87(10) | | 16(10) | 7(10) |
| | | 15 | 24(10) | 72(10) | | 2(10) | 10(10) |

[1]Replications consisted of individual Petri dishes containing 10 ECB larvae and one leaf.
[2]A. Significant difference between encapsulated-leaf watered and encapsulated pot-watered leaves.
B. Significant difference between encapsulated-pot watered and not encapsulated-pot watered leaves.
C. Significant difference between encapsulated-leaf watered and not encapsulated-leaf watered leaves.
D. Lumping watering treatments, significant difference between encapsulated and not encapsulated treatments.
[3]No. significant differences between not encapsulated-leaf watered and not encapsulated-pot watered leaves.

We claim:

1. A dispersible biocontrol formulation comprising a pregelatinized starchy material, a sugary material, and an effective amount of a biocontrol agent, wherein the relative amount of the starchy material with respect to the agent is sufficient to entrap the agent within a matrix of the starchy material upon drying of an aqueous dispersion of the formulation on a substrate treated with the dispersion, and wherein the amount of sugary material is sufficient to promote adherence of the dried dispersion on said substrate.

2. The formulation of claim 1 wherein the pregelatinized starchy material is pregelatinized corn starch.

3. The formulation of claim 1 wherein the pregelatinized starchy material is pregelatinized corn flour.

4. The formulation of claim 1 wherein the sugary material is selected from the group consisting of sucrose, glucose, fructose, mannose, α-methyl glucoside, and corn syrups.

5. The formulation of claim 1 wherein the biocontrol agent is a living pathogen selected from the group consisting of bacteria, fungi, yeasts, viruses, microsporidians, and protozoa.

6. The formulation of claim 5 wherein the biocontrol agent is *Bacillus thuringiensis*.

7. The formulation of claim 1 wherein said formulation is a dry mixture.

8. An adherent, autoencapsulating, sprayable, biocontrol formulation comprising an aqueous dispersion of a pregelatinized starchy material, a sugary material, and an effective amount of a biocontrol agent, wherein the relative amount of the starchy material with respect to the agent is sufficient to entrap the agent within a matrix of the starchy material upon drying of the dispersion on a substrate treated with the dispersion, and wherein the amount of sugary material is sufficient to promote adherence of the dried dispersion on said substrate.

9. The formulation of claim 8 wherein the pregelatinized starchy material is pregelatinized corn starch.

10. The formulation of claim 8 wherein the pregelatinized starchy material is pregelatinized corn flour.

11. The formulation of claim 8 wherein the sugary material is selected from the group consisting of sucrose, glucose, fructose, mannose, α-methyl glucoside, and corn syrups.

12. The formulation of claim 8 wherein the biocontrol agent is a living pathogen selected from the group consisting of bacteria, fungi, yeasts, viruses, microsporidians, and protozoa.

13. The formulation of claim 12 wherein the biocontrol agent is *Bacillus thuringiensis*.

14. The formulation of claim 1 and further comprising a dispersant for said pregelatinized starchy material.

15. The formulation of claim 8 and further comprising a dispersant for said pregelatinized starchy material.

* * * * *